United States Patent [19]

Asmussen et al.

[11] Patent Number: 4,810,195

[45] Date of Patent: Mar. 7, 1989

[54] CONDITIONING LIQUIDS FOR TOOTH OR BONE MATTER

[75] Inventors: Erik Asmussen, Farum; Erik C. Munksgaard, Kokkedal, both of Denmark

[73] Assignee: Bayer Aktiengesellschaft, Leverkusen, Fed. Rep. of Germany

[21] Appl. No.: 181,810

[22] Filed: Apr. 15, 1988

[30] Foreign Application Priority Data

Apr. 24, 1987 [DE] Fed. Rep. of Germany ....... 3713667

[51] Int. Cl.$^4$ .............................................. A61K 6/00
[52] U.S. Cl. ..................... 433/215; 433/229; 433/226
[58] Field of Search ................ 433/215–229

[56] References Cited

U.S. PATENT DOCUMENTS

| | | | |
|---|---|---|---|
| 3,936,939 | 2/1976 | Faunce | 433/9 |
| 4,010,545 | 3/1977 | Kilian et al. | 433/9 |
| 4,214,006 | 7/1980 | Thiele | 514/560 |
| 4,224,023 | 9/1980 | Cheung | 433/216 |
| 4,442,125 | 4/1984 | Thiele | 514/60 |
| 4,556,561 | 12/1985 | Brown et al. | 424/48 X |

*Primary Examiner*—Nancy A. B. Swisher
*Attorney, Agent, or Firm*—Sprung Horn Kramer & Woods

[57] ABSTRACT

A solution for conditioning tooth or bone matter for filling, containing an acid and an amphoteric amino compound, the solution having a pH from 0.1 to 3.5.

6 Claims, No Drawings

CONDITIONING LIQUIDS FOR TOOTH OR BONE MATTER

The invention relates to liquids for conditioning defective tooth or bone matter for treatment with plastic synthetic material.

Plastic synthetic materials which harden are used as filling materials in the treatment of cavities in tooth or bone matter, especially in the dental field. Acrylate-based fillings are in general preferred as the synthetic materials which harden. However, these polymeric fillings have the disadvantages that they do not stick well to the dentin or bone. To solve this problem, for example, partial undercuts have hitherto been made; for this, it was necessary to remove considerable amounts of fresh dentin beyond the affected region.

In order to avoid these disadvantages, the dentin or the bone has been pretreated in various ways in order to increase the adhesion of the synthetic material.

Thus, it is known to etch the dentin or the enamel surface with strong acids, for example phosphoric acid, and then to carry out the filling operation (Zidan et al., Scand. J. Dental Res. 88, 348 to 351 (1980)). Apart from the irritating effffect of the strong acid in the oral region, the adhesion of the filling is inadequate.

It is also known to pretreat the dentin with ethylenediamineacetic acid and then to treat it with a coating agent of an aliphatic aldehyde or a ketone and an olefinically unsaturated monomer, for example an ester of acrylic or methacrylic acid (European Pat. No. A 0,141,324 and European Pat. No. A 0,109,057).

Liquids for conditioning tooth or bone matter have been found, which contain, in aqueous solution, an acid with a $pK_A$ value of less than $+5$ and an amphoteric amino compound with a $pK_A$ value in the range from 3.9 to 12.5 and a $pK_B$ value in the range from 10.5 to 13.5, the solutions having a pH in the range from 0.1 to 3.5.

The new liquids according to the invention condition the tooth or bone matter before coating with a priming agent (primer or liner). A plastic synthetic material applied undergoes firm bonding with the tooth or bone matter pretreated in this way.

Acids for the liquids according to the invention have an acid strength [$pK_a$ value] of less than 5, preferably of $-9$ to $+5$. The solubility of the acids in water is in general greater than 0.5% by weight, preferably greater than 1% by weight.

The following acids may be mentioned as examples: pyruvic acid, citric acid, oxalic acid, phosphoric acid and nitric acid.

Amphoteric amino compounds for the liquids according to the invention have an acid strength [$pK_A$ value] in the range from 3.9 to 12.5, preferably 9.0 to 10.6, and a base strength [$pK_B$ value] in the range from 10.5 to 13.5, preferably 11.5 to 12.5.

Amphoteric amino compounds which may be mentioned as preferred are those of the formula

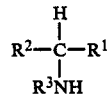

in which
$R^1$ represents a carboxyl group,
$R^2$ denotes hydrogen or a lower alkyl radical which is optionally substituted by hydroxyl, thio, methylthio, carboxyl, carboxamide, amino, phenyl, hydroxy-phenyl or the groups

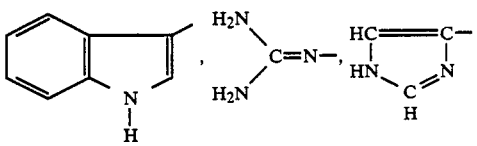

and
$R^3$ denotes hydrogen or phenyl, and wherein the radicals $R^1$ and $R^3$ can be linked via a propyl radical, or in which
$R^1$ represents hydrogen,
$R^2$ denotes the group $$-A-NH_3X$$

in which
A represents a divalent alkylene radical with 1 to 6 carbon atoms and
X represents halogen, and
$R^3$ denotes hydrogen.

The following amphoteric amino compounds may be mentioned as examples: glycine, serine, threonine, cysteine, thryosine, asparagine, glutamine, alanine, valine, leucine, isoleucine, proline, methionine, phenylalanine, tryptophane, lysine, arginine, histidine, N-phenylglycine, ethylenediamine hydrochloride, ethylenediamine hydrobromide, propylenediamine hydrochloride, propylenediamine hydrobromide, butylenediamine hydrochloride and butylenediamine hydrobromide.

Particularly preferred amphoteric amino compounds are glycine, phenylalanine, lysine and ethylenediamine hydrochloride.

A process has also been found for the preparation of liquids for conditioning tooth or bone matter, which is characterized in that an aqueous solution of an acid with a $pK_A$ value of less than 5 and an amphoteric amino compound with a $pK_a$ value in the range from 3.9 to 12.5 and a $pK_B$ value in the range from 10.5 to 13.5 are reacted, a pH in the range from 0.1 to 3.5 being maintained.

The pH for the process according to the invention can be maintained in a manner which is known per se, for example with the aid of suitable indicators or with the aid of potentiometric measurement methods (Ullman Volume 5, 926 to 936 (1980)).

The components are in general brought together with vigorous stirring in the preparation of the liquids according to the invention. The components are in general brought together at room temperature, for example in the temperature range from 0° to 30° C.

When used, the liquids according to the invention are applied to the defective tooth or bone matter, for example in a cavity. Cavities in the enamel or dentin may be mentioned here as preferred.

After the application of the liquids according to the invention, they are in general dried, for example with warm air.

Before treatment of the defective tooth or bone matter with the plastic synthetic material, coating with a primer material is preferably carried out after conditioning with the liquids according to the invention.

Priming materials such as are described in European Pat. No. A 0,141,324 European Pat. No. A 0,199,057 may be mentioned here in particular.

Priming materials which contain an aldehyde or a ketone and an unsaturated monomer with active hydrogen are particularly preferred.

Aldehydes which may be mentioned here are formaldehyde, compounds which can release formaldehyde, acetaldehyde, propionaldehyde, butyraldehyde and glutaraldehyde. Glutaraldehyde is particularly preferred.

Ketones which may be mentioned here are cyclopentanone, benzophenone, cyclohexanone, 2,4-pentanedione and camphorquinone. Camphorquinone is particularly preferred.

Olefinically unsaturated monomers with active hydrogen (Broensted acid) which may be mentioned here are acrylic acid esters, methacrylic acid esters and acrylic acid or methacrylic acid urethanes with OH, $NH_2$, NH, SH or PH groups. Hydroxyethyl methyacrylate is particularly preferred.

Priming materials which contain 1 to 50% by weight of an aliphatic aldehyde with 1 to 20 carbon atoms and 5 to 80% by weight of an olefinically unsaturated monomer with at least one active hydrogen atom in the form of OH, $NH_2$ or CH groups and, if appropriate, water and/or a toxicologically acceptable organic solvent are particularly preferred. The synthetic materials which harden are essentially determined by the field of use. Thus, for example, only monomers which are physiologically acceptable and can polymerize in the oral region can be used for the polymerization in the dental field. Such monomers for dental fillings are known per se (E. Asmussen, Plastflyldningsmaterialer Of Boghandel, Kopenhagen 1981).

Examples of synthetic materials which may be mentioned are compositions of acrylate and/or methacrylate monomers, suitable catalysts, starters, accelerators and fillers.

Conditioning of the defective tooth or bone matter with the liquids according to the invention gives, surprisingly, a basis for treatment with synthetic materials which guarantees a long life and high strength of the repair.

EXAMPLES 1 TO 35 (PREPARATION)

The solutions according to the invention (Examples 1 to 21) are prepared by taking either the acid or the amphoteric amine and adding the other component, with vigorous stirring, such that the pH according to the invention is established.

The following Table 1 shows liquids according to the invention in Examples 1 to 21 and 25 to 35 and comparison substances in Examples 22 to 24.

TABLE 1

| Example No. | Liquid for conditioning | pH |
|---|---|---|
| 1 | 33.0% by weight of phosphoric acid 61.3% by weight of water, 5.7% by weight of N—phenyl-glycine | 0.2 |
| 2 | 2.4% by weight of nitric acid, 91.9% by weight of water, 5.7% by weight of N—phenyl-glycine | 1.0 |
| 3 | 9.6% by weight of pyruvic acid, 86.4% by weight of water, 4.0% by weight of N—phenyl-glycine | 1.5 |
| 4 | 18.0% by weight of phosphoric acid, 76.1% by weight of water 5.9% by weight of glycine | 1.5 |

TABLE 1-continued

| Example No. | Liquid for conditioning | pH |
|---|---|---|
| 5 | 9.1% by weight of pyruvic acid, 81.8% by weight of water 9.1% by weight of lysine hydrochloride | 1.9 |
| 6 | 9.1% by weight of pyruvic acid 81.8% by weight of water 9.1% by weight of glycine | 2.8 |
| 7 | 19.2% by weight of citric acid 66.0% by weight of water 14.8% by weight of glycine | 2.8 |
| 8 | 19.2% by weight of citric acid, 69.9% by weight of water 10.9% by weight of glycine | 2.6 |
| 9 | 19.2% by weight of citric acid, 74.6% by weight of water 6.2% by weight of glycine | 2.4 |
| 10 | 19.2% by weight of citric acid, 77.1% by weight of water 3.7% by weight of glycine | 2.2 |
| 11 | 19.2% by weight of citric acid, 79.0% by weight of water 1.8% by weight of glycine | 2.0 |
| 12 | 9.1% by weight of pyruvic acid 81.8% by weight of water 9.1% by weight of glycine | 2.4 |
| 13 | 9.1% by weight of pyruvic acid, 81.8% by weight of water 9.1% by weight of ethylenediamine hydrochloride | |
| 14 | 8.4% by weight of phosphoric acid, 80.0% by weight of water 11.6% by weight of glycine | 2.2 |
| 15 | 6% by weight of acetic acid, 86% by weight of water 8% by weight of glycine | |
| 16 | 10% by weight of tartaric acid, 82% by weight of water 8% by weight of glycine | 2.8 |
| 17 | 10% by weight of tartaric acid, 85% by weight of water 5% by weight of glycine | 2.4 |
| 18 | 10% by weight of tartaric acid, 88% by weight of water 2% by weight of glycine | 2.2 |
| 19 | 10% by weight of malic acid, 81% by weight of water 9% by weight of glycine | 2.8 |
| 20 | 10% by weight of malic acid, 84% by weight of water 6% by weight of glycine | 2.4 |
| 21 | 10% by weight of malic acid, 87% by weight of water 3% by weight of glycine | 2.0 |
| For comparison | | |
| 22 | 35% by weight of phosphoric acid, 65% by weight of water | 0.1 |
| 23 | 10% by weight of pyruvic acid 90% by weight of water | 1.0 |
| 24 | 15% by weight of ethylenediamine tetraacetic acid | 7.4 |
| 25 | 19.2% by weight of citric acid 79.0% by weight of water 1.8% by weight of glycine | 2.0 |
| 26 | 19.2% by weight of citric acid 77.1% by weight of water 3.7% by weight of glycine | 2.2 |
| 27 | 19.2% by weight of citric acid 74.6% by weight of water 6.2% by weight of glycine | 2.4 |
| 28 | 19.2% by weight of citric acid 66.0% by weight of water 14.8% by weight of glycine | 2.8 |
| 29 | 9.6% by weight of pyruvic acid 86.0% by weight of water 4.4% by weight of glycine | 2.0 |
| 30 | 9.2% by weight of pyruvic acid 82.4% by weight of water 8.4% by weight of glycine | 2.4 |
| 31 | 8.5% by weight of pyruvic acid 76.1% by weight of water | 2.8 |

TABLE 1-continued

| Example No. | Liquid for conditioning | pH |
|---|---|---|
| 32 | 15.4% by weight of glycine<br>9.5% by weight of maleic acid<br>86.0% by weight of water | 2.0 |
| 33 | 4.5% by weight of glycine<br>9.4% by weight of maleic acid<br>84.5% by weight of water | 2.4 |
| 34 | 6.1% by weight of glycine<br>9.2% by weight of maleic acid<br>82.9% by weight of water | 2.8 |
| 35 | 7.9% by weight of olycine<br>10.0% by weight of oxalic acid<br>78.0% by weight of water<br>12.0% by weight of glycine | 2.4 |

EXAMPLE 36 (COATING AGENT)

A formulation of 5% by weight of glutaraldehyde, 35% by weight of hydroxyethyl methacrylate and 60% by weight of water is used as the coating agent.

EXAMPLE 37 (TESTING OF THE BONDING STRENGTH)

The bonding strength (shear strength) between the dentin or enamel and a commercially available synthetic filling composition is measured in the example.

Human teeth which have been extracted and kept in the moist state are used for the test. The teeth are embedded by casting in epoxy resin; a smooth surface is produced by wet grinding. Final grinding is carried out with carbon paper 1000.

Examples Nos. 1 to 6 and 22, 23 and 24 were measured in accordance with the method of Bowen [J. Dent. Res. 1965, 44, 690 to 695].

Other examples were measured in accordance with the method of Munksgaard, Iric & Asmussen [J. Dent. Res. 64 (12), 1409 to 1411 (1985)].

A commercially available synthetic filling composition was used.

The surface was then treated with a liquid of Examples 1 to 35 for 60 seconds in each case. The treated area is then rinsed with distilled water and dried with air.

The area conditioned with the liquids of Examples 1 to 35 is then treated with the coating agent according to Example 36 for 60 seconds. The area is then dried with air.

The shear strength on dentin is summarized in Table 2 and that on enamel in Table 3.

TABLE 2

| Liquid according to Example No. | 1 | 2 | 3 | 4 | 5 | 6 | 7 | 8 | 9 | 10 | 11 | 12 | 13 |
|---|---|---|---|---|---|---|---|---|---|---|---|---|---|
| Shear strength (MPa) | 6.1 ± 2.0 | 13.8 ± 3.2 | 10.7 ± 4.4 | 6.9 ± 2.2 | 8.2 ± 3.7 | 13.2 ± 4.4 | 21.6 | 20.9 | 29.7 | 19.9 | 18.9 | 15.0 | 9.9 |

| Liquid according to Example No. | 14 | 15 | 16 | 17 | 18 | 19 | 20 | 21 | 22 | Comparison 23 | 24 | 26 | |
|---|---|---|---|---|---|---|---|---|---|---|---|---|---|
| Shear strength (MPa) | 15.5 | 5.6 | 12.3 | 10.6 | 8.8 | 9.5 | 12.7 | 10.9 | 1.9 ± 0.9 | 3.9 ± 1.3 | 13.4 ± 2.9 | 16.8 ± 5.6 | 14.6 ± 6.7 |

| Liquid according to Example No. | 27 | 28 | 29 | 30 | 31 | 32 | 33 | 34 | 35 |
|---|---|---|---|---|---|---|---|---|---|
| Shear strength (MPa) | 14.7 ± 3.4 | 18.9 ± 2.2 | 8.8 ± 2.5 | 10.6 ± 4.6 | 12.3 ± 4.5 | 10.9 ± 2.5 | 12.7 ± 1.4 | 9.5 ± 2.3 | 5.4 ± 3.1 |

TABLE 3

| Liquid according to Example No. | 2 | 6 | 7 | 8 | 9 | 10 | 11 | 25 | 27 | 28 | 29 | 30 | 31 |
|---|---|---|---|---|---|---|---|---|---|---|---|---|---|
| Shear strength (MPa) | 23.7 ± 3.6 | 24.7 ± 4.3 | 13.1 | 14.9 | 17.1 | 20.5 | 24.3 | 10.7 ± 0.9 | 9.9 ± 2.4 | 8.4 ± 1.3 | 16.4 ± 2.7 | 13.6 ± 1.8 | 10.5 ± 1.7 |

It will be understood that the specification and examples are illustrative but not limitative of the present invention and that other embodiments within the spirit and scope of the invention will suggest themselves to those skilled in the art.

We claim:

1. A solution for conditioning tooth or bone matter comprising an aqueous solution of an acid with a $pK_A$ value of less than +5 and of an amphoteric amino compound with a $pK_A$ value from 3.9 to 12.5 and a $pK_B$ value from 10.5 to 13.5, the solution having a pH from 0.1 to 3.5.

2. A solution according to claim 1, wherein the acid has a $pK_A$ value from −9 to +5.

3. A solution according to claim 1, wherein the amphoteric amino compound has a $pK_A$ value from 9.0 to 10.6 and a $pK_B$ value from 11.5 to 12.5.

4. A solution according to claim 1 having a pH from 1.5 to 2.5.

5. In the filling of a tooth with a plastic filling material wherein the dentin of the tooth to be filled is pretreated with a liquid, and the treated tooth is then filled, the improvement which comprises employing as the pretreatment liquid a solution according to claim 1.

6. The process according to claim 5, wherein between the pretreatment and the filling the tooth is coated.

* * * * *